United States Patent
Au

(10) Patent No.: US 12,296,162 B2
(45) Date of Patent: May 13, 2025

(54) METHODS TO REDUCE FLASHES ON ELECTRODES

(71) Applicants: GALVANI BIOELECTRONICS LIMITED, Brentford (GB); Cindy Au, Brentford (GB)

(72) Inventor: Cindy Au, Brentford (GB)

(73) Assignee: GALVANI BIOELECTRONICS LIMITED, Stevenage (GB)

(*) Notice: Subject to any disclaimer, the term of this patent is extended or adjusted under 35 U.S.C. 154(b) by 624 days.

(21) Appl. No.: 17/595,169

(22) PCT Filed: May 7, 2020

(86) PCT No.: PCT/US2020/031797
§ 371 (c)(1),
(2) Date: Nov. 10, 2021

(87) PCT Pub. No.: WO2020/231729
PCT Pub. Date: Nov. 19, 2020

(65) Prior Publication Data
US 2022/0355102 A1 Nov. 10, 2022

Related U.S. Application Data

(60) Provisional application No. 62/846,546, filed on May 10, 2019.

(51) Int. Cl.
*A61N 1/05* (2006.01)
*B29C 45/14* (2006.01)
(Continued)

(52) U.S. Cl.
CPC ...... *A61N 1/0551* (2013.01); *B29C 45/14344* (2013.01); *B29C 45/1671* (2013.01); *B29K 2083/00* (2013.01); *B29L 2031/753* (2013.01)

(58) Field of Classification Search
CPC ............... A61N 1/0551; A61N 1/0556; B29C 45/14344; B29C 45/1671; B29C 45/0001;
(Continued)

(56) References Cited

U.S. PATENT DOCUMENTS 3,752,151 A * 8/1973 Robichaud ............. A61B 5/251
600/394
3,841,312 A * 10/1974 Corasanti ................. A61B 5/25
600/397
(Continued)

FOREIGN PATENT DOCUMENTS

WO 2019020986 A1 1/2019

OTHER PUBLICATIONS

Lee, 'Polyurethan Reaction Injection Molding: Process, Materials, and Properties', Rubber Chemistry and Technology, vol. 53, issue 3, 1980, pp. 542-599.
(Continued)

*Primary Examiner* — Mark W. Bockelman
(74) *Attorney, Agent, or Firm* — Merchant & Gould P.C.

(57) ABSTRACT

A method for use in making an electrode assembly (20) comprises the steps of applying an electrode (24) on a first layer of material (22); laser welding a lead (23) to the electrode; applying an adhesive backfill (26) over the electrode and the lead; and applying a second layer of material (28) over the adhesive backfill and a portion of the first layer to prevent a leakage path between the electrode and the second layer.

20 Claims, 3 Drawing Sheets

(51) Int. Cl.
*B29C 45/16* (2006.01)
*B29K 83/00* (2006.01)
*B29L 31/00* (2006.01)

(58) Field of Classification Search
CPC .......... B29C 45/14639; B29K 2083/00; B29L 2031/753; B29L 2031/34
See application file for complete search history.

(56) References Cited

U.S. PATENT DOCUMENTS

| | | | | |
|---|---|---|---|---|
| 4,300,153 | A * | 11/1981 | Hayakawa | H01L 21/56 257/E23.125 |
| 5,647,105 | A * | 7/1997 | Candotti | A44B 17/0088 24/691 |
| 7,996,092 | B2 | 8/2011 | Mrva et al. | |
| 2006/0271137 | A1 | 11/2006 | Stanton-Hicks | |
| 2007/0092352 | A1 * | 4/2007 | Nilsen | F16B 41/005 411/5 |
| 2008/0172116 | A1 | 7/2008 | Mrva et al. | |
| 2010/0047376 | A1 | 2/2010 | Imbeau | |
| 2014/0135882 | A1 | 5/2014 | Prasannakumar et al. | |
| 2015/0174396 | A1 | 6/2015 | Lee | |

OTHER PUBLICATIONS

Extended European Search Report received for EP Application No. EP20806742 on Jan. 2, 2023, 7 pgs.
International Search Report and Written Opinion received for PCT Application No. PCT/US2020/031797, 8 pgs.
International Preliminary Report on Patentability received for PCT Application No. PCT/US2020/031797, 6 pgs.
Injection molding of liquid silicon rubber, Wikipedia, Jan. 30, 2019, p. 3, [retrieved Jan. 27, 2023, via <https://en.wikipedia.org/w/index.php?title=Injection_molding_of_liquid_silicone_rubber&oldid=880969158>].

* cited by examiner

METHODS TO REDUCE FLASHES ON ELECTRODES

RELATED APPLICATION

The present application is National Phase entry of PCT Application No. PCT/US2020/031797, filed May 7, 2020, which claims the benefit of U.S. Provisional Application No. 62/846,546 filed May 10, 2019, which is hereby incorporated herein in its entirety by reference.

TECHNICAL FIELD

The disclosed disclosure relates generally to the field of electrodes, and more particularly, but not exclusively, to electrodes employed in the field of neuromodulation.

BACKGROUND

The electrochemical performance of an electrode is one of the highest priority areas for optimization of leads and cuffs for use in neuromodulation and other applications. In neuromodulation, high performing electrodes lead to achieving safe and efficacious delivery of therapy. Ensuring that the electrode is high performing takes more than material selection and development. Even if electrode material and its charge injection capability have been optimized for the target therapy, the leads may still fail to achieve target electrochemical performance when the charge injection surfaces are blocked by contaminants or other non-conductive manufacturing residues. In scenarios where there are silicone flashes on the charge injection surfaces of the electrodes from the lead manufacturing and assembly process, the electrochemical performance can be highly compromised and variable from lead to lead, making it challenging to tune the system to optimize for the therapy.

Known solutions for addressing this problem have shortcomings. One solution is the use of thin film technology to integrate the electrode onto the substrate directly, skipping the molding step entirely. The disadvantages of this approach are that thin film materials are not soft enough and are not as well-proven as silicone for chronic implant applications. Furthermore, this presents less manufacturing freedom to fine tune the three-dimensional form factor of the neural interface device (e.g., a cuff or a paddle electrode) to fit highly variable anatomy and demographics of patients.

SUMMARY

A detailed failure analysis by the inventors revealed that the electrodes can be partially covered in silicone flashes from the molding process. These silicone "flashes" that cover the electrode surface reduce the effective surface area through which therapy can be delivered. Silicone flash may occur as a result of pressurized and heated silicone leaking around the edges of the electrode during manufacturing.

The present disclosure addresses the problems discussed and describes an inventive electrode assembly and method of making an electrode assembly. According to an embodiment, a method for use in making an electrode assembly comprises the steps of assembling electrode(s) onto a first-shot of molded silicone with positioning-assist windows; tagging down the electrode in place with implant-grade adhesive, electrically connecting the electrode(s) via laser or resistance welding with an intermediate electrically conductive wire or coil; applying an adhesive backfill over the electrode(s) and interconnect; and applying a second-shot of material over the adhesive backfill and electrodes.

In one particular embodiment, the first-shot, second-shot, and adhesive backfill may all be comprised of silicone, but different materials may be used for each shot as well as the backfill. In addition, the first-shot may hold the electrodes or electrode pads in their desired position with blind pockets formed to match their profile. The second-shot, injected during high-pressure molding, may be applied after the adhesive backfill has cured. The adhesive backfill material may be applied such that it seals off any gap between the metal electrodes and first-shot, preventing silicone from the second-shot molding to lead through the cracks to get on top of the electrode on the tissue facing surface.

In an embodiment, there is provided a method for use in making an implantable electrode assembly for neuromodulation, comprising: forming a first layer of material including a hole formed therein; positioning an electrode in the hole in the first layer of material; connecting an electrical lead to the electrode; applying a backfill material over the electrode, the electrical lead connection, and a portion of the first layer sufficient to seal any gap between the electrode and the hole; and applying a second layer of material over the backfill material.

In an embodiment, there is provided an electrode assembly, comprising: a first layer of material having a hole formed therein; an electrode connectable to a lead configured to fit within the hole; a backfill applied over the electrode and any exposed portion of the lead and an electrical connection between the electrode and the lead; and a second layer of material applied over the backfill and a portion of the first layer; and wherein the backfill fills any opening between the electrode and the first layer, thereby blocking any leakage path between the electrode and the second layer that could cover a portion of an exposed surface of the electrode.

In an embodiment, there is provided an electrode assembly for neuromodulation, comprising: a first layer of material having an opening; an electrode connectable to a lead provided at least partly in the opening; a backfill provided over the electrode, the backfill covering an edge of the electrode and at least a part of an electrical connection between the electrode and the lead; and a second layer of material provided over the backfill and a portion of the first layer, wherein the backfill blocks any opening between the electrode and the first layer for reducing leakage path between a target contact surface of the electrode and the second layer.

Detailed features of the disclosure are set forth below.

DETAILED DESCRIPTION OF ILLUSTRATIVE EMBODIMENTS

The disclosure relates to systems and devices for stimulating a nerve intra- or extra-venously through use of an implantable device that includes one or more electrodes positioned toward the distal end of a lead or within a neural interface device, including a cuff or a flat paddle lead, implanted within or around the outside of a blood vessel, for example an artery, a vein or nerve or a bundle of nerves such that the electrodes are in contact with surface tissue. Stimulation of the nerve may be defined by the delivery of electricity (e.g., electrical pulses) to a neuron, a nerve cell, a nerve bundle, or other target location of the nervous system that excites the neuron, nerve cell, nerve bundle, or other target location.

Figure 1A:
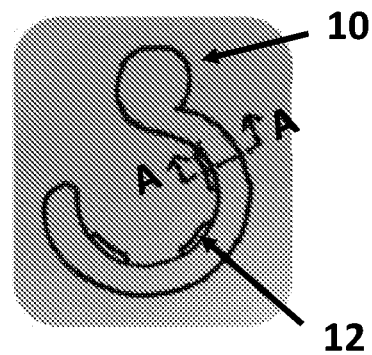
FIG. 1A is a cross-sectional view of an example implantable device cuffed about a nerve bundle.

FIG. 1A depicts an example system including an implantable device 10 formed of a flexible, biocompatible material, such as a biocompatible thermoplastic elastomer, a soft polymer substrate, etc., that may be used to stimulate a nerve using current induced in the implantable device by a source 12 (not otherwise shown in FIG. 1). The implantable device 10 show in FIG. 1A is an extra-vascular device in the form of a cuff that is wrapped around a nerve or blood vessel (not shown). The implantable device 10 is merely provided as an example and may come in many different shapes, configurations, sizes, etc. For example, the implantable device is not required to be fully wrapped around a target, may be paddle-like and used in both extravascular and intravascular applications, or other configurations for stimulating nerve tissue.

The implantable device 10 may include one or more electrodes 12, sensors or arrays of the same, each array comprising one or more sets of electrodes or sensors. In some embodiments, each electrode 12 may be configured to emit electrical fields to stimulate a nerve proximate to the implantable device 10. Each set of electrodes 12 within electrode array may include one or more individual electrodes for this purpose.

Each electrode 12 (or a set of such electrodes, etc.) may be coupled to an electrically conductive wire or coil lead 30 (FIG. 2), such as a micro-coil lead, made substantially out of conductive material to a high-density, flexible interconnection (not shown). In some embodiments, for example, the conductive wire or coil leads 30 may be comprised substantially (e.g., 90 or 95 percent by weight) out of metals such as platinum, stainless steel (e.g., MP35N or titanium. Other metals, such as gold, may also be used. As depicted in FIG. 1, the electrode 12 may be connected in series and/or parallel to other electrodes to provide multiple channels for increased selectivity of the parameters of the emitted electric field (e.g., magnitude, direction, location, etc.). In some embodiments, this arrangement may provide for more targeted and efficient stimulation of a nerve.

The electrode 12 may be coupled through the leads 30 to one or more other components (not shown) of implantable device 10, such as a main lead body for the neural interface device, a control circuit, a battery, capacitive storage and/or other chargeable storage elements, etc., as necessary or desirable. In an embodiment, each electrode 12 is connected (i.e., welded or other suitable technique) to a lead 30 and then connected to a flexible interconnection lead (not shown) of the neural interface device 10. The interconnection lead can connect directly to the lead body or provide an electrical connection between the leads 30, either in series or parallel as desired. The lead 30 may be a micro-coil or other suitably flexible lead. The interconnection lead can also (and/or alternatively) connect directly to the lead body or provide an electrical connection between the electrodes 12, either in series or parallel as desired. The interconnection lead may be a micro-coil or other suitably flexible lead. Thus, in some embodiments, the lead 30 may refer to both the lead 30 and the interconnection lead. In other embodiments, the lead 30 may be comprised solely of interconnection leads. In other embodiments, the lead 30 may be comprised solely of interconnection leads between electrodes 12 and comprised of an interconnection lead as a portion of lead 30 connectable to the lead body.

The electrode 12 may be a sensor or array of sensors that measure a physical or temporal parameter associated with implantable device 10 and/or its surroundings. For example, in one embodiment, the set of sensors may include sensors for measuring the electrical potential between two points. In addition, the set of sensors may include other sensors for measuring other characteristics such as pressure, temperature, time, resistance, conductance, electrical/magnetic flux, and so forth. Each sensor in the set of sensors may be coupled to any other component of implantable device 10, such as the control circuit, the electrodes 12, energy sources, etc.

Each of the components of implantable device 10 may be formed within or affixed into the soft polymer substrate 14 so that the substrate supports the formed or affixed components. In certain embodiments, the substrate 14 may comprise a single piece of flexible polymer material, such as silicone, to facilitate implantation into a patient and manipulation therein. In some embodiments, the substrate 14 may comprise a plurality of layers of material with various components, such as electrode 12 or arrays, sensors and wires or coils 30 positioned between the layers. In an embodiment, a first layer may be formed in a mold in which heated silicone is injected under pressure, i.e., "shot" into the mold. A series of holes in the first-shot layer may be formed by the mold or cut into the first layer once it has cured. Once the holes have been created, one or more electrodes may be placed in each whole, with each electrode then be connected to the wires or coils 30, typically by welding the lead to a back of the electrode. Once the electrodes and leads are welded, a second-shot layer of heated and pressurized flexible polymer material may be placed over the back of the electrodes to seal the electrodes between the first-shot and second-shot layers and maintain their positions within their respective holes.

Figure 1B:
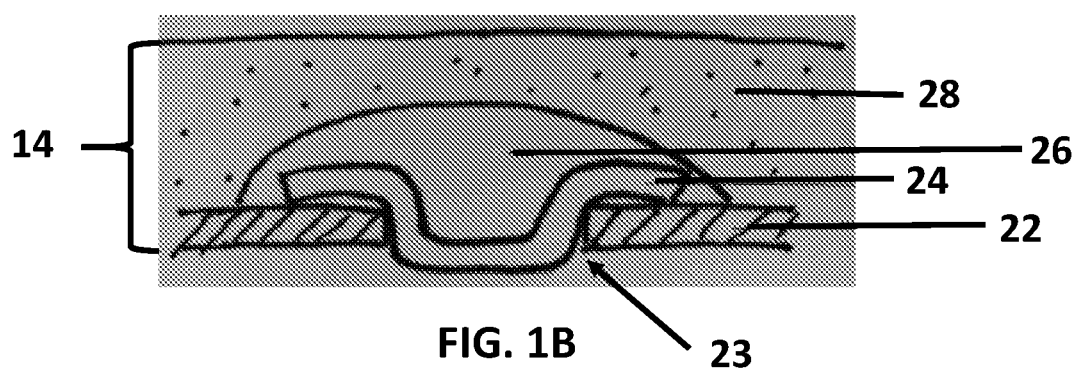
FIG. 1B is a plan view and cross-sectional view of an electrode assembly made in accordance with the present disclosure.

The following method has been found to be consistently effective at preventing silicone flashes of the kind described above. FIG. 1B is a cross-section along the line A-A of FIG. 1A. As shown in FIG. 1B, a first layer 22 of material, which may be a first-shot of silicone, polymer, or biocompatible thermoplastic elastomer material, or biocompatible thermoplastic polyurethane. The first layer 22 of material may be configured to include one or more holes 23, each of which may hold a metal electrode 24 in a desired position. The electrode 24 is positioned in the hole 23 so that a front side of the electrode is approximately co-planar with an exposed surface of the first layer 22. A backfill 26 of material, such as a silicone adhesive, may then be overlaid on the backside of electrode 24 without using heat or pressure, or at least without using pressure so as to form a seal over the electrode and a portion of the first layer, thereby closing any remaining opening between the electrode 24 and the first layer 22 around the edges of the hole 23. A second layer 28 of material like the first layer may then be applied over the backfill 26.

The backfill 26 may comprise a material of different hardness compared to that of the first layer 22 and the second layer 28. For example, the backfill 26 may comprise a softer (or less stiff) material compared to the first layer 22 and the second layer 28. In one example, the hardness of the first layer 22 and the second layer 28 may be around 50 Shores A-90 Shores A, favourably 60-85 Shores A, favourably 70-80 Shores A; and the hardness of the backfill 26 may be ≥30 Shores A, favourably ≥25 Shores A, favourably ≥20 Shores A, favourably ≥15 Shores, favourably ≥10 Shores (e.g. measured using a shore durometer).

In an embodiment, instead of using a first layer and a second layer of the same material, each layer may be of a different material. For example, the first layer may be made of a stiffer durometer of silicone or polymeric material so that it is more difficult for the metal electrode to tear through the first layer and potential cut into the neurovascular bundle (NVB) to which the neural interface devices is being applied. The second layer may then be of a different material with different stiffness or the same material (silicone) with lower durometer configured to elicit more favorable tissue reaction or to help the neural interface device form factor be more pliable, which may be beneficial for lowering the pressure exerted on the NVB, and thereby reduce the risk of mechanically induced tissue damage. In the event two layers of different materials or stiffness are utilized, it is desirable to prevent the two layers from mixing uncontrollably because variations in mechanical modulus distribution can lead to the neural interface device that may deform due in unpredictable ways due to a buildup in residual stress. An improved control of the two layers can be achieved by using the method of manufacture described in this disclosure.

Figure 2:
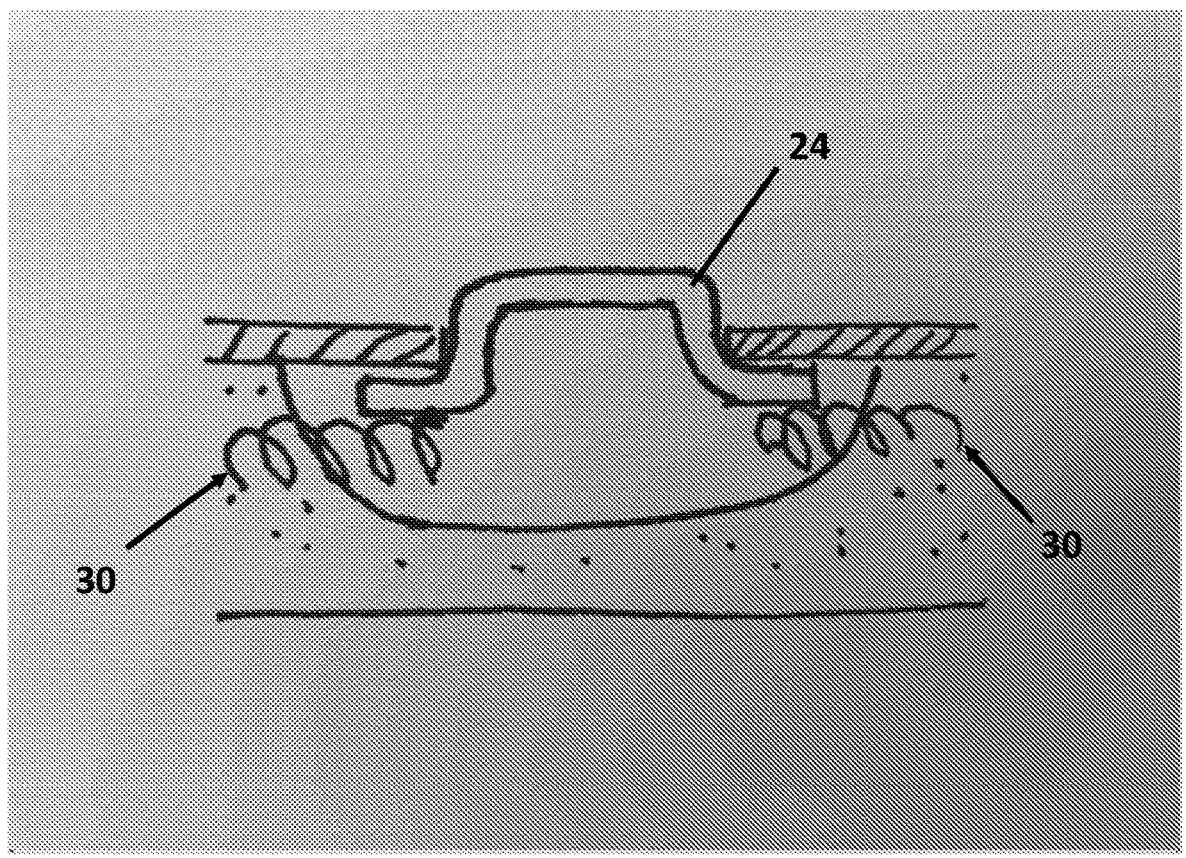
FIG. 2 is a plan view and cross-section view of an electrode assembly and conductive wires in accordance with the present disclosure.

The backfill 26 may be applied after connecting the electrode 24 to a lead 30 as shown in FIG. 2. The lead 30 may be connected to the electrode 24 using laser welding or other suitable technique and provide an electrical connection between the electrode and a lead body (not shown) or an interconnection lead as described above. For example, at least one of the following may be used for an electrical connection between the lead and the electrode: welding (laser or resistance), crimping and conductive adhesive.

Applying the backfill 26 over the lead connection to the electrode 24 may serve to further secure the lead connection over time. The second layer 28 of material may be applied only after the backfill 26 is cured.

Figure 3:
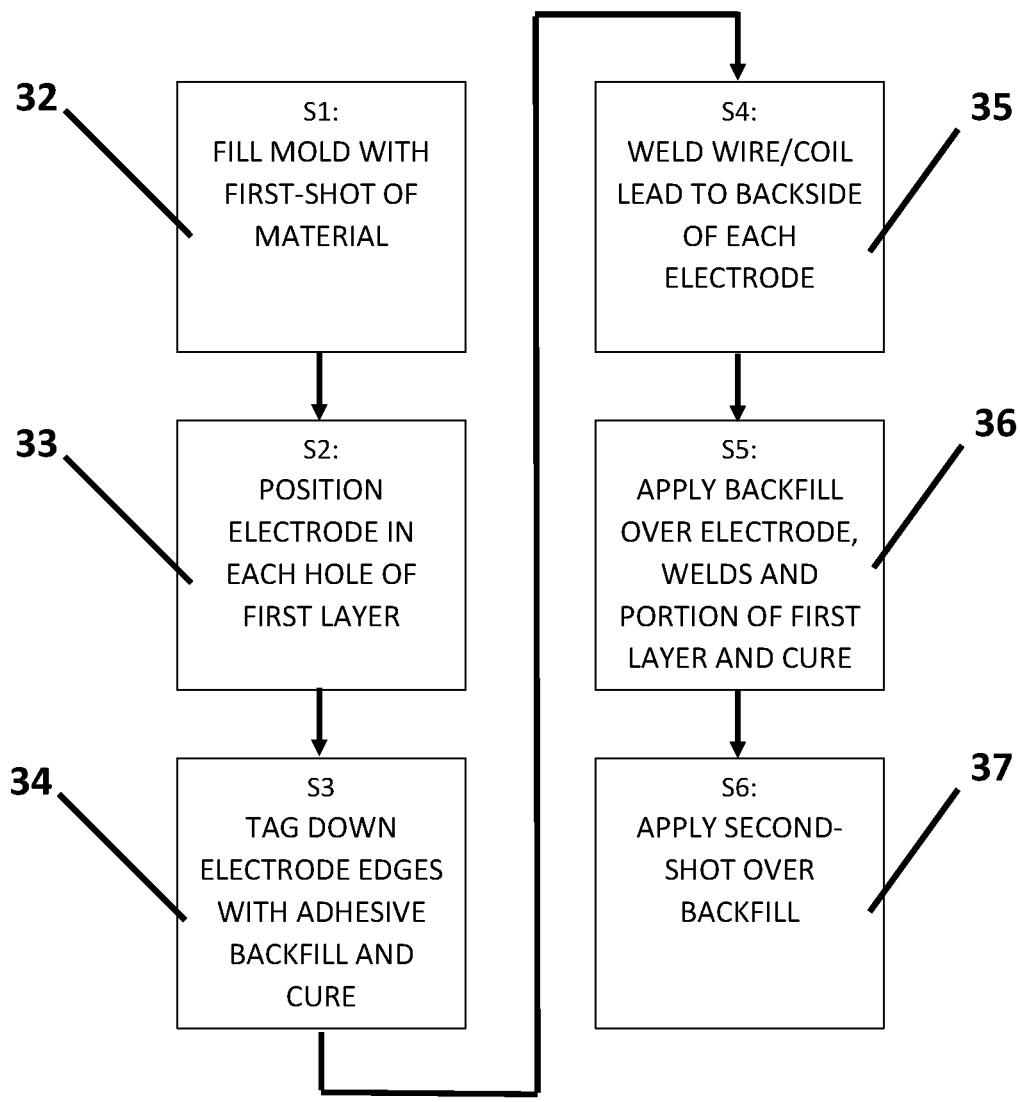
FIG. 3 is a flowchart of a method for making an electrode assembly in accordance with the present disclosure.

Referring to FIG. 3, a method of manufacturing an electrode assembly in accordance with the present disclosure includes the steps denoted S1 through S6:

S1 32: Create a first layer of material of a neuro-stimulation device, such as by filling a mold with a first-shot of material, such as silicone, to form the first layer. The first layer may include a number of holes either formed by the mold or cut out of the first layer after being molded.

S2 33: Position one or more electrodes in each of the holes of the first layer.

S3 34: Apply a backfill material, such as silicone adhesive, to the one or more electrodes in each hole along edges of the electrode where welding of the coil will not take place in order to hold the electrode in place for welding. The backfill material may be applied in a small amount. Ensure the backfill material is properly cured by following the adhesive manufacturer's curing profile, which may be moisture-cured or UV-cured.

S4 35: Weld or otherwise connect a lead or similar device to a backside or interconnection point of each of the one or more electrodes to form a physical and electrical connection between the electrode and the lead.

S5 36: Apply a backfill over the backside of the electrode, and welded interconnection points or exposed lead, and a portion of the first layer so as to form a complete seal between the electrode, the lead and the hole, thereby preventing a leakage path between the backside and frontside of the electrode. Ensure proper curing of the adhesive as noted in S3.

S6 37: Position the backfilled first layer in a mold and applying a second-shot of silicone material over the backside of the electrode to complete the neuro-stimulation device.

Other biocompatible materials may be used in place of silicone, such as other biocompatible polymers. Likewise, different biocompatible materials may be used as a backfill versus only silicone adhesive.

Furthermore, it will be appreciated by the skilled in the art that whilst the above manufacturing steps have been presented as an example, some orders of the manufacturing steps may be varied. For example, the order of steps S2 33 to S5 36 may be changed such that the step of connecting an electrical lead to the electrode (e.g. S4 35) happens before the backfill material is applied (e.g. S3 34), or before the electrode is placed in the holes (electrode positioning window) in the first layer (e.g. S2 33), or even before the first layer is created (e.g. S1 32). In other words, a pre-connected (e.g. welded) electrode and electrical lead sub-assembly may be provided before the electrode is placed in the holes in the first layer, or before the backfill material is applied, or even before the first layer is formed.

In addition to or as an alternative to the above, the following examples consistent with the present teachings are set out in the following numbered clauses:

1. A method for use in making an implantable electrode assembly (20) for neuromodulation, comprising:
    forming a first layer of material (22) including a hole (23) formed therein;
    positioning an electrode (24) in the hole in the first layer of material;
    connecting an electrical lead (30) to the electrode;
    applying a backfill material (26) over the electrode, the electrical lead connection, and a portion of the first layer sufficient to seal any gap between the electrode and the hole; and
    applying a second layer of material (28) over the backfill material.

2. The method of clause 1, wherein one or more of the first layer of material and the second layer of material is formed by a first-shot and a second-shot of a heated and pressurized polymer material.

3. The method of clause 2, wherein the material of either the first layer, formed by the first-shot, or the second layer, formed by the second-shot, comprises silicone.

4. The method of clause 2, wherein one or more of the first layer of material and the second layer of material comprises a biocompatible thermoplastic elastomer.

5. The method of clause 1, wherein the backfill material comprises adhesive silicone.

6. The method of clause 1, wherein the combination of the first layer of material and the hole holds each electrode in a desired position.

7. The method of clause 6, further comprising, prior to connecting, apply a second backfill material between an edge of the electrode and the hole in order to hold the electrode in place for connecting.

8. The method of clause 7, wherein the second backfill material comprises adhesive silicone.

9. The method of clause 7, further comprising, prior to applying the backfill material, curing the second backfill material.

10. The method of clause 1, further comprising, prior to applying the second layer of material, curing the backfill material.

11. The method of clause 1, wherein applying the second layer of material comprises a high-pressure injection.

12. The method of clause 1, wherein the backfill material blocks any leakage path between the electrode and the second layer of material, and wherein the second layer of material is one of a heated and pressurized polymer material and a heated and pressurized flexible thermoplastic elastomer.

13. The method of clause 1, wherein the first layer of material is different from the second layer of material.

14. The method of clause 1, wherein the first layer of material has a first hardness and the second layer of material has a second hardness, and wherein the first hardness and the second hardness are different.

15. The method of clause 1, wherein connecting an electrical lead to the electrode includes connecting one end of a flexible lead to the electrode and an opposite end of the flexible lead to a lead body.

16. The method of clause 15, wherein the flexible lead is a micro-coil.

17. The method of clause 1, wherein connecting an electrical lead to the electrode includes connecting one end of an interconnection lead to the electrode and an opposite end of the interconnection lead to a lead body.

18. The method of clause 1, wherein connecting an electrical lead to the electrode includes connecting one end of a flexible lead to the electrode and an opposite end of the flexible lead to an interconnection lead.

19. The method of clause 18, wherein the interconnection lead is connected to a second flexible lead connected to a second electrode.

20. The method of clause 18, wherein the interconnection lead is connected to a lead body.

21. An electrode assembly, comprising:
  a first layer of material having a hole formed therein;
  an electrode configured to fit within the hole
  a lead welded to the electrode;
  an adhesive backfill applied over the electrode and any exposed portion of the lead and weld; and
  a second layer of material applied over the adhesive backfill and a portion of the first layer;
  wherein the first layer is configured to hold the electrode in a desired position;
  wherein the second layer comprises a high-pressure application; and
  wherein the adhesive backfill fills any opening between the electrode and the first layer, thereby blocking any leakage path between the electrode and the second layer that could cover a portion of an exposed surface of the electrode.

22. The electrode assembly of clause 21, wherein the first layer or mater, the backfill and second layer of material is one or more of silicone, a polymer and a biocompatible thermoplastic elastomer.

23. The electrode assembly of clause 22, wherein the first layer of material and the second layer of material are the same.

24. The electrode assembly of clause 22, wherein the first layer of material and the second layer of material are different.

25. The electrode assembly of clause 24, wherein the first layer of material has a first hardness and the second layer of material has a second hardness, and wherein the first harness and the second harness are different.

26. The electrode assembly of clause 21, further comprising a second adhesive backfill material applied to an edge of the electrode and the hole in order to the electrode in a desired position prior to application of the weld.

27. The electrode assembly of clause 26, wherein the adhesive backfill is applied after the second adhesive backfill material has cured.

28. The electrode assembly of clause 21, wherein the second layer is applied after the backfill has cured.

29. The method of clause 21, wherein the lead welded to the electrode is a flexible lead having one end welded to the electrode and an opposite end of the flexible lead connected to a lead body.

30. The method of clause 29, wherein the flexible lead is a micro-coil.

31. The method of clause 21, wherein the lead welded to the electrode is an interconnection lead having one end welded to the electrode and an opposite end connected to a lead body.

32. The method of clause 21, wherein the lead welded to the electrode is a flexible lead having one end welded to the electrode and an opposite end connected to an interconnection lead.

33. The method of clause 32, wherein the interconnection lead is connected to a second flexible lead welded to a second electrode.

34. The method of clause 32, wherein the interconnection lead is connected to a lead body.

35. A method for use in making an implantable electrode assembly (20) for neuromodulation, comprising:
  connecting an electrical lead (30) to the electrode;
  forming a first layer of material (22) including a hole (23) formed therein;
  positioning an electrode (24) in the hole in the first layer of material;
  applying a backfill material (26) over the electrode, the electrical lead connection, and a portion of the first layer sufficient to seal any gap between the electrode and the hole; and
  applying a second layer of material (28) over the backfill material.

36. A method for use in making an implantable electrode assembly (20) for neuromodulation, comprising:
  forming a first layer of material (22) including a hole (23) formed therein;
  connecting an electrical lead (30) to the electrode;
  positioning an electrode (24) in the hole in the first layer of material;
  applying a backfill material (26) over the electrode, the electrical lead connection, and a portion of the first layer sufficient to seal any gap between the electrode and the hole; and
  applying a second layer of material (28) over the backfill material.

The foregoing description of the examples, including illustrated examples, of the invention has been presented only for the purpose of illustration and description and is not intended to be exhaustive or to limit the invention to the precise forms disclosed. Numerous modifications, adaptations, and uses thereof will be apparent to those skilled in the art without departing from the scope of this invention. The illustrative examples described above are given to introduce the reader to the general subject matter discussed here and are not intended to limit the scope of the disclosed concepts

What is claimed:

1. A method for use in making an implantable electrode assembly for neuromodulation, comprising:

forming a first layer of material including a hole formed therein;
positioning an electrode in the hole in the first layer of material;
connecting an electrical lead to the electrode;
applying a backfill material over the electrode, the electrical lead connection, and a portion of the first layer sufficient to seal any gap between the electrode and the hole; and
applying a second layer of material over the backfill material.

2. The method of claim 1, wherein one or more of the first layer of material and the second layer of material is formed by a first-shot and a second-shot of a heated and pressurized polymer material.

3. The method of claim 1, wherein the backfill material comprises adhesive silicone.

4. The method of claim 1, further comprising, prior to connecting, applying a second backfill material between an edge of the electrode and the hole to hold the electrode in place for connecting.

5. The method of claim 4, further comprising, prior to applying the backfill material, curing the second backfill material.

6. The method of claim 1, further comprising, prior to applying the second layer of material, curing the backfill material.

7. The method of claim 1, wherein the backfill material blocks any leakage path between the electrode and the second layer of material.

8. The method of claim 1, wherein the first layer of material has a first hardness and the second layer of material has a second hardness, and wherein the first hardness and the second hardness are different.

9. The method of claim 1, wherein the backfill is softer than the first layer and the second layer.

10. An electrode assembly for neuromodulation, comprising:
a first layer of material comprising an opening;
an electrode connectable to a lead provided at least partly in the opening;
a backfill provided over the electrode, the backfill covering an edge of the electrode; and
a second layer of material provided over the backfill and a portion of the first layer, wherein the backfill blocks any gap between the electrode and the first layer for reducing leakage path between a target contact surface of the electrode and the second layer.

11. The electrode assembly according to claim 10, further wherein the backfill covers at least a part of an electrical connection between the electrode and the lead.

12. The electrode assembly of claim 10, wherein the backfill comprises adhesive silicone.

13. The electrode assembly of claim 10, wherein the backfill covers a peripheral edge of the electrode.

14. The electrode assembly of claim 10, wherein the first layer of material, the backfill, and the second layer of material are formed from one or more of silicone, a polymer, and a biocompatible thermoplastic elastomer.

15. The electrode assembly of claim 10, wherein the first layer of material and the second layer of material are the same.

16. The electrode assembly of claim 10, wherein the first layer of material has a first hardness and the second layer of material has a second hardness, and wherein the first hardness and the second hardness are different.

17. The electrode assembly of claim 10, further comprising a second adhesive backfill material applied to a second edge of the electrode and the opening.

18. The electrode assembly of claim 10, further comprising multiple electrodes, wherein the electrodes are connected by a flexible interconnection lead.

19. The electrode assembly of claim 18, wherein the backfill covers the flexible interconnection lead.

20. The electrode assembly of claim 19, wherein the backfill is softer than the first layer and the second layer.

* * * * *